US012053171B2

(12) United States Patent
Palese et al.

(10) Patent No.: US 12,053,171 B2
(45) Date of Patent: Aug. 6, 2024

(54) KNOTLESS IMPLANTS, INSTRUMENTS, AND METHODS

(71) Applicant: Biomet Sports Medicine, LLC, Warsaw, IN (US)

(72) Inventors: Christopher M. Palese, Warsaw, IN (US); Daniel R. Norton, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 610 days.

(21) Appl. No.: 17/142,935

(22) Filed: Jan. 6, 2021

(65) Prior Publication Data

US 2021/0121171 A1 Apr. 29, 2021

Related U.S. Application Data

(62) Division of application No. 15/897,254, filed on Feb. 15, 2018, now Pat. No. 10,912,550.

(Continued)

(51) Int. Cl.

*A61B 17/04* (2006.01)
*A61B 17/00* (2006.01)
*A61B 90/00* (2016.01)

(52) U.S. Cl.

CPC .................... *A61B 17/0401* (2013.01); *A61B 2017/00367* (2013.01); *A61B 2017/0409* (2013.01);

(Continued)

(58) Field of Classification Search

CPC .............. A61B 17/0401; A61B 17/864; A61B 2017/0409; A61B 2017/0412; A61B 2017/044; A61B 2017/0445; A61B 2017/0459; A61F 2/0811; A61F 2002/0858; A61F 2002/0888

See application file for complete search history.

(56) References Cited

U.S. PATENT DOCUMENTS 8,075,588 B2 12/2011 Berberich
2002/0161401 A1* 10/2002 Steiner .............. A61B 17/0401 606/232

(Continued)

OTHER PUBLICATIONS

"U.S. Appl. No. 15/897,254, Corrected Notice of Allowability mailed Nov. 18, 2020", 7 pgs.

(Continued)

*Primary Examiner* — Martin T Ton
(74) *Attorney, Agent, or Firm* — Schwegman Lundberg & Woessner, P.A.

(57) ABSTRACT

A suture anchor and methods of use thereof are disclosed. The suture anchor comprises an anchor body having a slot formed in the body and a passage extending through the body in a first direction. The passage is sized to permit a suture to traverse the body through the passage. The suture anchor also has a shaft with a sharp portion, and the slot and the passage intersect within the anchor body. The shaft is movable relative to the anchor body within the slot from a first position in which the sharp portion and the passage do not intersect, to a second position in which the sharp portion and the passage intersect. The shaft can penetrate a suture or multiple suture strands to fix the suture or suture strands relative to the suture anchor.

18 Claims, 5 Drawing Sheets

Related U.S. Application Data

(60) Provisional application No. 62/462,182, filed on Feb. 22, 2017.

(52) U.S. Cl.
CPC ................. *A61B 2017/0414* (2013.01); *A61B 2017/0427* (2013.01); *A61B 2017/0437* (2013.01); *A61B 2017/0448* (2013.01); *A61B 2017/045* (2013.01); *A61B 2017/0451* (2013.01); *A61B 2017/0456* (2013.01); *A61B 2090/037* (2016.02)

(56) References Cited

U.S. PATENT DOCUMENTS

2004/0133239 A1* 7/2004 Singhatat ........... A61B 17/0401 606/232
2011/0004242 A1* 1/2011 Stchur ................ A61B 17/0401 606/232
2012/0296345 A1* 11/2012 Wack ................. A61B 17/0401 606/228
2013/0204298 A1* 8/2013 Graul ................. A61B 17/0401 606/232
2014/0257381 A1 9/2014 Palese
2016/0213370 A1 7/2016 Chan et al.
2018/0235595 A1 8/2018 Palese et al.

OTHER PUBLICATIONS

"U.S. Appl. No. 15/897,254, Final Office Action mailed Jul. 22, 2020", 13 pgs.
"U.S. Appl. No. 15/897,254, Non Final Office Action mailed Jan. 9, 2020", 12 pgs.
"U.S. Appl. No. 15/897,254, Notice of Allowance mailed Oct. 5, 2020", 11 pgs.
"U.S. Appl. No. 15/897,254, Response filed Apr. 9, 2020 to Non Final Office Action mailed Jan. 9, 2020", 12 pgs.
"U.S. Appl. No. 15/897,254, Response filed Sep. 21, 2020 to Final Office Action mailed Jul. 22, 2020", 9 pgs.
"U.S. Appl. No. 15/897,254, Response filed Nov. 11, 2019 to Restriction Requirement mailed Sep. 9, 2019". 6 pgs.
"U.S. Appl. No. 15/897,254. Restriction Requirement mailed Sep. 9, 2019", 6 pgs.

* cited by examiner

KNOTLESS IMPLANTS, INSTRUMENTS, AND METHODS

CLAIM OF PRIORITY

This application is a division of U.S. application Ser. No. 15/897,254, filed Feb. 15, 2018, which claims the benefit of U.S. Provisional Patent Application Ser. No. 62/462,182, filed on Feb. 22, 2017, the benefit of priority of each of which is claimed hereby, and each of which is incorporated by reference herein in its entirety.

FIELD OF THE DISCLOSURE

The present disclosure relates to surgical implant systems, including implants, instruments, and methods for installing an implant. Specifically, the present disclosure relates to knotless implants, also referred to as suture anchors, for securing soft tissue to bone.

BACKGROUND

Various implant systems have been created for repairing soft-tissue damage in different surgical contexts. As an example, suture anchors have been utilized to repair tears to a patient's labrum in the shoulder or hip, or a tear to a patient's meniscus in the knee. In some cases, the suture anchor is driven into a pre-drilled bone hole, and suture is passed through the particular soft tissue in order to tension the suture construct and draw the tissue back into its normal anatomical position against the bone. At the end of the repair, a knot can be used to assist in drawing the torn soft tissue back to its anatomically-correct position and/or to secure the tissue in position. However, the use of knots to repair soft-tissue tears can result in a number of issues for the patient. For example, knot migration can occur after the initial repair whereby the position of the knot moves during normal physical motion by the patient. In the case of a labrum repair in the shoulder, for example, if the knot migrates far enough, it can become interposed between the glenoid and the humerus and potentially cause chondral abrasion and discomfort or more serious issues for the patient. Further, knot loosening can also occur resulting in an ineffective repair causing the soft tissue to move out of position and not heal correctly.

Knotless suture anchors have also been developed, but such anchors suffer from deficiencies in securing the suture relative to the anchor. Often, a friction-lock is used in which the suture is pressed against the anchor in an attempt to secure the suture relative to the anchor. Of course, such constructs can suffer from slippage and loss of tension between the suture and the anchor at the point of the friction-lock.

The presently disclosed subject matter seeks to address numerous issues with knotted and knotless suture anchors by proving improved knotless implants, instruments, and methods.

SUMMARY

To better illustrate the system disclosed herein, a non-limiting list of examples is provided here:

Example 1 is a suture anchor comprising: an anchor body having a slot formed in the body and a passage extending through the body in a first direction, the passage being sized to permit a suture to traverse the body through the passage; and a shaft with a sharp portion, wherein the slot and the passage intersect within the anchor body, the shaft being movable relative to the anchor body within the slot from a first position in which the sharp portion and the passage do not intersect, to a second position in which the sharp portion and the passage intersect.

In Example 2, the subject matter of Example 1 optionally includes wherein the passage defines first and second openings in first and second sides of the anchor body through which the suture can extend.

In Example 3, the subject matter of any one or more of Examples 1-2 optionally include an eyelet having a first eyelet portion and a second eyelet portion, wherein a maximum dimension of the first eyelet portion is greater than a maximum dimension of the second eyelet portion.

In Example 4, the subject matter of Example 3 optionally includes wherein a junction is formed between the second eyelet portion and the passage, the junction being configured to permit movement of the suture from the second eyelet portion into the passage across the junction.

In Example 5, the subject matter of Example 4 optionally includes wherein the junction is a portion of the anchor body joining the second eyelet portion and the passage, which is breakable upon application of a predetermined force against the junction by the suture.

In Example 6, the subject matter of any one or more of Examples 3-5 optionally include means for allowing passage of the suture from the second eyelet portion into the passage upon application of a predetermined amount of tension on the suture.

In Example 7, the subject matter of any one or more of Examples 1-6 optionally include wherein the shaft is lockable relative to the anchor body within the slot by way of a locking mechanism.

In Example 8, the subject matter of any one or more of Examples 1-7 optionally include wherein the shaft has a diameter and an enlarged section with a diameter that is greater than the diameter of the shaft, the enlarged section forming a step, and wherein a maximum cross-sectional width of the slot is less than the diameter of the enlarged section so that the enlarged section cannot travel into the slot.

In Example 9, the subject matter of Example 8 optionally includes wherein the anchor body comprises a retaining cavity defining a step configured to engage with the step of the enlarged section and prevent the shaft from backing out of the slot.

Example 10 is a system comprising the suture anchor of any of Examples 1-9 and a suture, wherein the passage has a width that is anywhere between about 100-150% of a cross-sectional diameter of the suture.

Example 11 is a suture anchor comprising: an anchor body having a suture eyelet and a passage extending through the body in a first direction, both the eyelet and the passage being sized to permit a suture to traverse the body therethrough, wherein a junction is formed between the eyelet and the passage that is configured to permit movement of the suture from the eyelet into the passage across the junction.

In Example 12, the subject matter of Example 11 optionally includes wherein the anchor body further comprises a slot and the suture anchor further comprises a shaft with a sharp portion, wherein the slot and the passage intersect within the anchor body, the shaft being movable relative to the anchor body within the slot from a first position in which the sharp portion and the passage do not intersect, to a second position in which the sharp portion and the passage intersect.

In Example 13, the subject matter of any one or more of Examples 11-12 optionally include wherein the eyelet comprises a first eyelet portion and a second eyelet portion, wherein a maximum dimension of the first eyelet portion is greater than a maximum dimension of the second eyelet portion.

In Example 14, the subject matter of Example 13 optionally includes wherein the junction is formed between the second eyelet portion and the passage.

In Example 15, the subject matter of any one or more of Examples 11-14 optionally include wherein the junction comprises a piece of material interposed between the eyelet and the passage that is arranged to engage the suture and allow the suture to pass by the piece of material upon application of a predetermined amount of tension to the suture.

Example 16 is a system comprising the suture anchor of any of Examples 11-15 and a suture, wherein the passage has a width that is anywhere between 100-150% of a cross-sectional diameter of the suture.

Example 17 is a method of repairing a tear in human tissue comprising: passing a suture through soft tissue of a patient and through an eyelet of a suture anchor; implanting the suture anchor into an opening formed in a bone of the patient; tensioning a free end of the suture to move the soft tissue and at least partially reduce the tear; and moving a shaft relative to and within the suture anchor so that the shaft penetrates through the suture and fixes the suture relative to the suture anchor.

In Example 18, the subject matter of Example 17 optionally includes wherein the shaft includes a sharp portion and the method comprises penetrating the suture with the sharp portion.

In Example 19, the subject matter of any one or more of Examples 17-18 optionally include locking the shaft relative to the suture anchor.

In Example 20, the subject matter of any one or more of Examples 17-19 optionally include applying a predetermined amount of tension to the free end of the suture so that the suture moves from the eyelet into a separate passage extending through the suture anchor.

In Example 21, the subject matter of Example 20 optionally includes preventing the suture from moving from the eyelet into the separate passage if the predetermined amount of tension on the free end of the suture is not met.

In Example 22, the subject matter of any one or more of Examples 20-21 optionally include passing multiple suture strands through the eyelet; tensioning free ends of the suture strands so that the suture strands move from the eyelet into the separate passage and become aligned within the separate passage; and moving the shaft relative to and within the suture anchor so that the shaft penetrates through the suture strands and fixes the suture strands relative to the suture anchor.

BRIEF DESCRIPTION OF THE FIGURES

The above-mentioned and other features and advantages of this disclosure, and the manner of attaining them, will become more apparent and the disclosure itself will be better understood by reference to the following description of examples taken in conjunction with the accompanying drawings, wherein.

Corresponding reference characters indicate corresponding parts throughout the several views. The exemplifications set out herein illustrate examples of the disclosure, and such exemplifications are not to be construed as limiting the scope of the disclosure any manner.

DETAILED DESCRIPTION

In describing the examples of the presently-disclosed subject matter illustrated and to be described with respect to the drawings, specific terminology will be used for the sake of clarity. However, the disclosure is not intended to be limited to any specific terms used herein, and it is to be understood that each specific term includes all technical equivalents.

As used herein, the following directional definitions apply. Anterior and posterior mean nearer the front or nearer the rear of the body, respectively, proximal and distal mean nearer to or further from the root of a structure, respectively, and medial and lateral mean nearer the sagittal plane or further from the sagittal plane, respectively. The sagittal plane is an imaginary vertical plane through the middle of the body that divides the body into right and left halves. In addition, the terms implant and prosthesis, and variations thereof, can be used interchangeably.

Figures 1A, 1B:
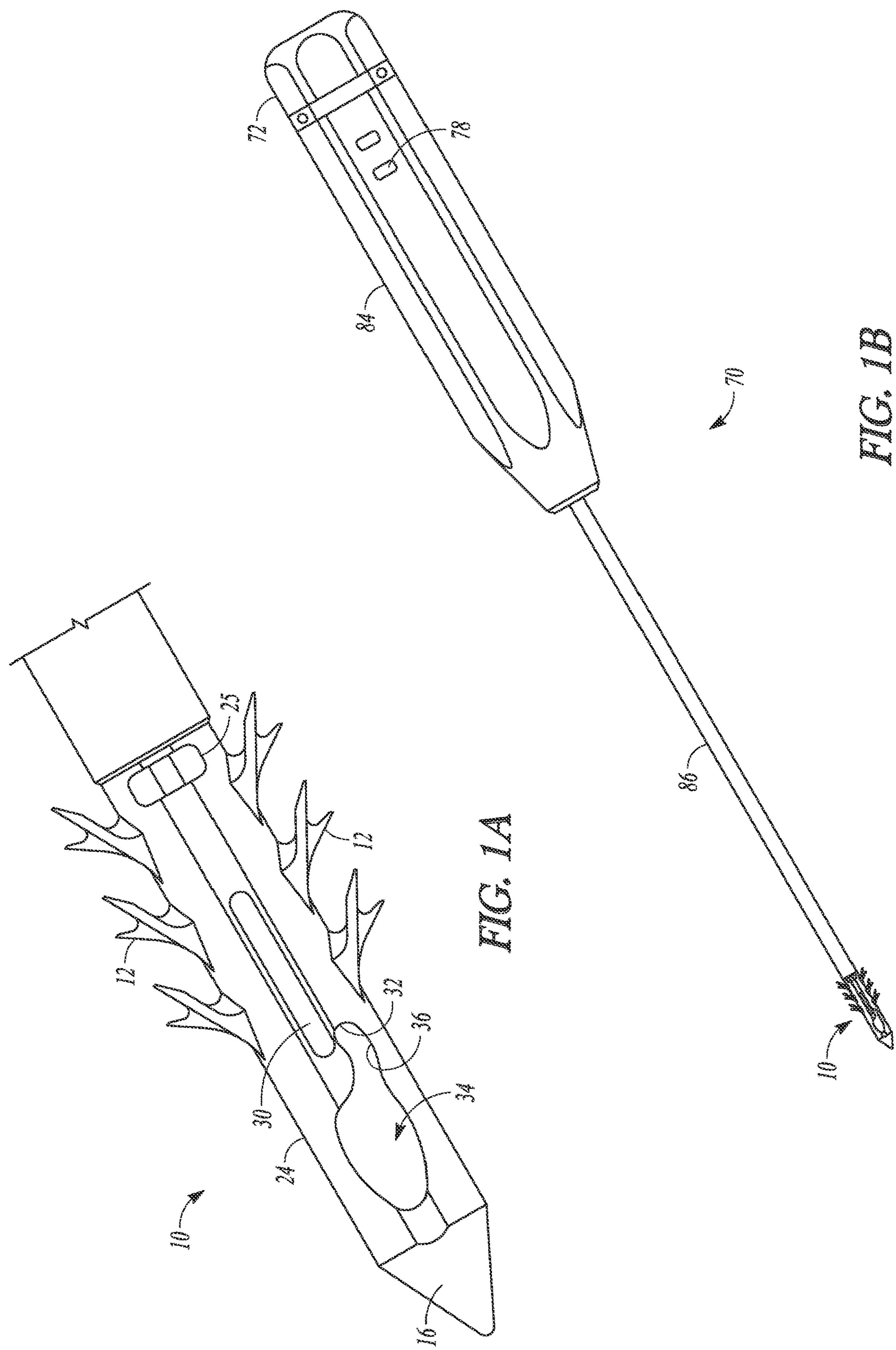
FIG. 1A illustrates a knotless implant in accordance with an example of the disclosure.
FIG. 1B illustrates the implant of FIG. 1A attached to a deployment instrument.

Referring to FIG. 1A, a knotless implant or suture anchor 10 is shown. Knotless suture anchor 10 can be used in various surgical procedures, including to repair soft-tissue tears. Merely as examples, knotless implant 10 can be used to repair tears of the labrum in the hip or shoulder, tears of the meniscus in the knee, rotator cuff tears, or soft-tissue tears in the small bones, such as in the hand or foot (e.g., collateral ligament repair, scapholunate repair, etc.). Stated another way, knotless anchor 10 can be used in any context where soft tissue is to be fixed to bone for proper reattachment. As anchor 10 is a knotless anchor, it does not suffer from many of the deficiencies associated with soft-tissue repairs that utilize a knot. In addition, anchor 10 can include an improved mechanism for securing suture relative to anchor 10.

Figure 1C:
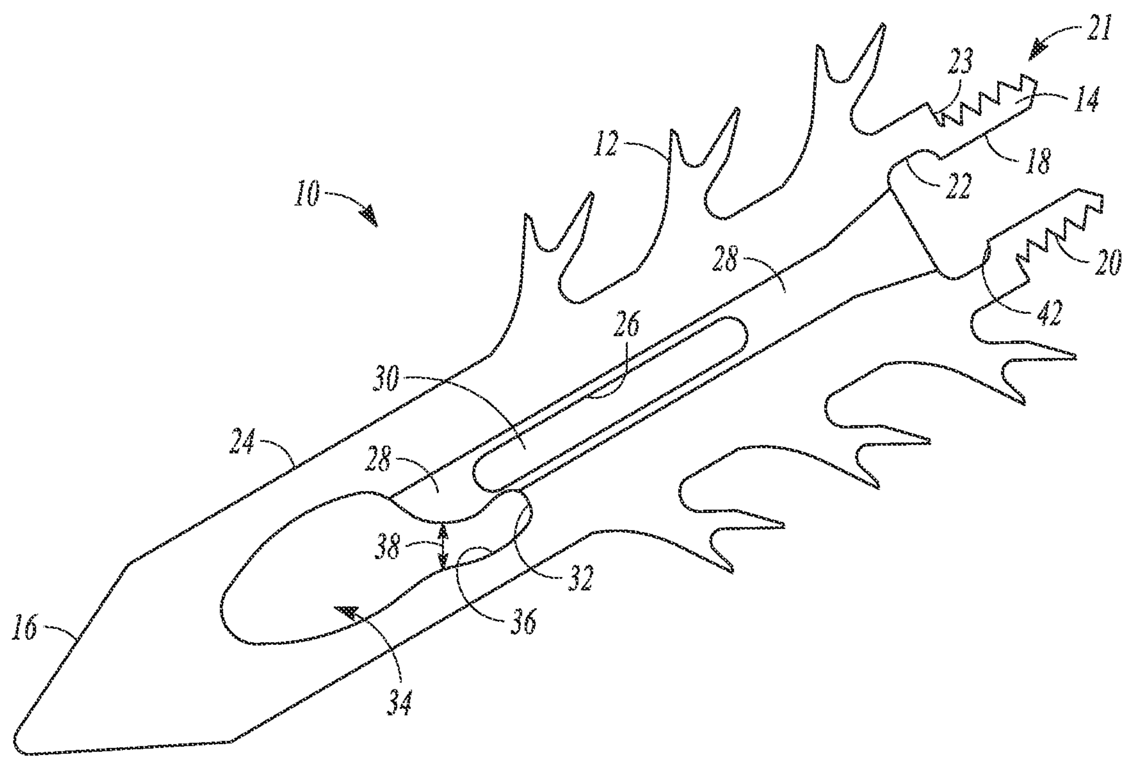
FIG. 1C is a cross-sectional view of the implant of FIG. 1A without the deployment instrument attached.

FIGS. 1A and 1C illustrate knotless implant 10 in a side and cross-sectional view, and show a body 24 of implant 10 as having spikes or barbs 12, optionally flexible, protruding from body 24. Although barbs 12 are shown, any alternative fixation mechanism can be used, including for example knurled or ridged surfaces, threading on body 24, roughened surfaces, ribs, circumferential grooves extending around part or all of the circumference of body 24, or the like. In an example, barbs 12 can be configured to flex when implant 10 is inserted into a bore formed in bone. Barbs 12 can therefore act to provide an outward force sufficient to penetrate the walls of the bore so as to prevent implant 10 from backing out of the bore.

Implant 10 can also include a distal section 16 without barbs, spikes, or another fixation mechanism. Distal section 16 can be tapered to a point at a distal-most end of implant 10 for easy insertion into the above-mentioned bone bore. As shown in FIG. 1A, distal section 16 can therefore form a substantially conical shape, in an example.

Figure 3A:
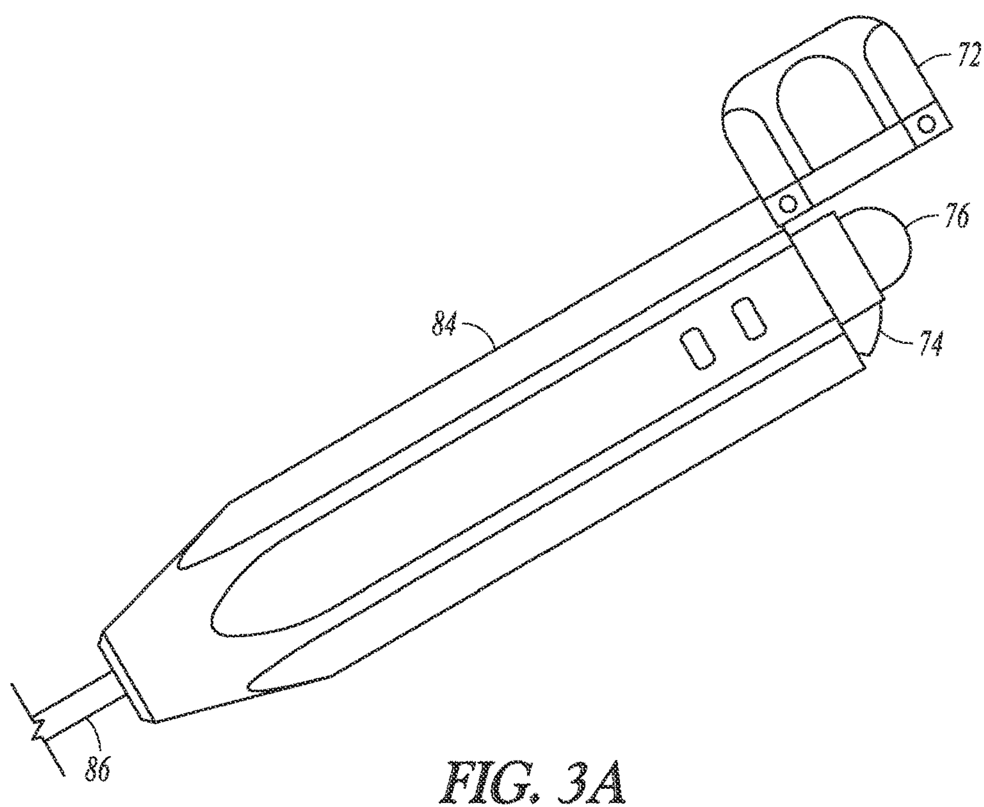
FIG. 3A is a perspective view of a handle of the deployment instrument of FIG. 1B shown in an undeployed state.
Figure 3B:
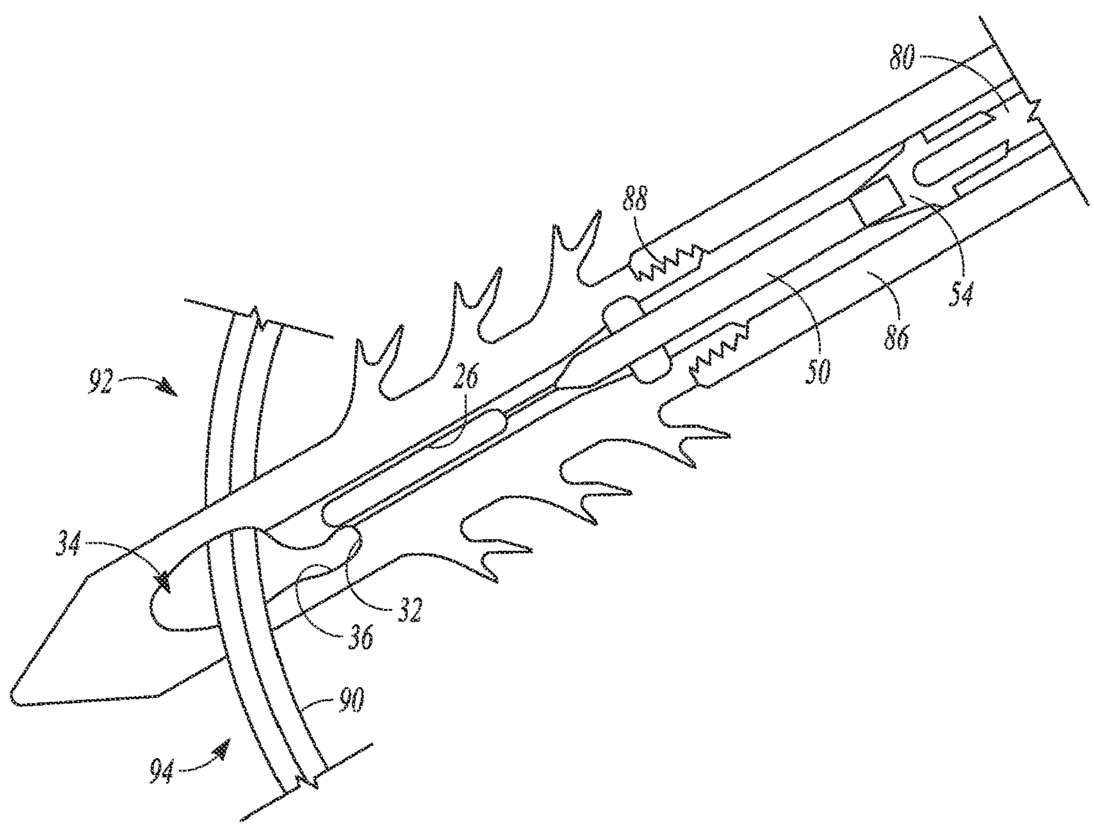
FIG. 3B is a cross-sectional view of the knotless implant of FIG. 1A shown in a corresponding undeployed state.

A large eyelet portion 34 sized to receive one (1) or more suture sections 90 (e.g., as shown in FIG. 3B) can be positioned adjacent distal section 16. It is to be understood that suture sections 90 depict, schematically, parts of the same suture or separate sutures altogether (i.e., depending upon the type of repair being conducted). For instance, in the case of a single-row rotator cuff repair, suture sections 90 can be portions of the same suture, as described in more detail below in the context of an exemplary surgical method.

In an example, large eyelet portion 34 can be sized to receive one (1), two (2), three (3), four (4), or even more than four (4) suture sections 90. Large eyelet portion 34 can transition into a small eyelet portion 36 formed through body 24 of implant 10 adjacent its distal section 16. Collectively, large eyelet portion 34 and small eyelet portion 36 can define an organ-like shape that forms a continuous single eyelet. Stated another way, large eyelet portion 34 can have a maximum cross-sectional dimension and small eyelet portion 36 can also have a maximum cross-sectional dimension, where the maximum dimension of small eyelet portion 36 is smaller than that of large eyelet portion 34. This difference in dimensions can act to create a neck region 38 between eyelet portions 34, 36 that, as explained in more detail below, causes suture sections 90 to move towards small eyelet portion 36 when tensioned. Neck region 38 can also facilitate alignment of suture sections 90 within small eyelet portion 36. In this regard, small eyelet portion 36 can have a cross-sectional width that is only slightly larger than the width of suture sections 90 so that, as suture sections 90 are tensioned, such sections 90 become linearly aligned in small eyelet portion 36.

Referring still to FIGS. 1A and 1C, an end of small eyelet portion 36 can form a frangible or breakable area 32, which is capable of being fractured when a certain amount of tension is applied to suture sections 90, and thus a certain amount of force is borne on breakable area 32. In the depicted example, breakable area 32 can be a solid piece of connected material forming an end part of small eyelet portion 36 that is capable of being broken by suture sections 90. As an example, to allow breakable area 32 the capability of fracturing, it can simply be a thin piece of material between small eyelet portion 36 and a vertical slot 26 of implant 10 and/or breakable area 32 can be scored or etched so that it breaks at a particular location, easily, when a predetermined amount of force is applied to breakable area 32.

In an alternate example, breakable area 32 can instead already be pre-broken and/or slightly open so that suture sections 90 can pass through area 32 into vertical slot 26 of implant 10. In such an example, flexible or non-flexible portions of body 24 (e.g., tabs) can come close together at the end of small eyelet portion 36 and optionally overlap or be spaced apart by a small distance (e.g., a distance equal to or slightly smaller than the cross-sectional diameter of suture sections 90) so that suture sections 90 can pass by the tabs when a certain amount of tension is applied to sections 90. In the case of non-flexible portions, such portions of body 24 can be spaced apart by a distance that is equal to or less than the cross-sectional diameter of suture sections 90 so that sections 90 must be forced through area 32 by exerting a certain amount of tension thereon. In this example, suture sections 32 cannot pass by the non-flexible portions of body 24 unless the appropriate tension is applied to suture sections 32 because the distance separating the non-flexible portions can be less than the cross-sectional diameter of suture sections 90. In another example, area 32 can instead be a single flexible tab that flexes to allow sutures 90 to pass by the tab. The single flexible tab can entirely close off area 32, could be spaced a distance away from a non-flexible part of area 32 (e.g., a non-flexible part of the wall defining small eyelet portion 36), or could overlap a portion of area 32, such as the wall defining small eyelet portion 36.

Because of breakable area 32, a surgeon can be offered tactile feedback that suture sections 90 have passed into vertical slot 26, for example by feeling resistance at breakable area 32 and then feeling suture sections 90 pass breakable area 32 into vertical slot 26. Thus, breakable area 32 can be any mechanism or means for preventing suture sections 90 from entering vertical slot 26 prematurely (e.g., during insertion of implant 10 with suture sections 90 into bone) and then allowing suture sections 90 to pass into vertical slot 26 and providing tactile confirmation of the same.

Adjacent breakable area 32 can be a vertical slot 26 of implant 10 that extends a distance along and through body 24. As described in more detail below, vertical slot 26 can be designed to align one (1) or more suture sections 90 linearly, as shown for instance in FIG. 4B, so that a spike 50 can be accurately driven through sutures 90. Thus, vertical slot 26 can have a maximum dimension that is roughly the same as the cross-sectional diameter of suture sections 90, optionally a maximum dimension that is only slightly larger than the cross-sectional diameter of suture sections 90. In practice, vertical slot 26 can have a maximum dimension that is anywhere between one-hundred to three hundred percent (100-300%), and more preferably one-hundred to one-hundred and fifty percent (100-150%) of the cross-sectional diameter of suture sections 90 Such dimensions can act to align suture sections 90 in a linear stacked arrangement in vertical slot 26.

Vertical slot 26 can also traverse completely through body 24 of implant 10 in a first direction, so as to form a passage with openings 30 on the sides of implant 10. Suture sections 90 can pass within body 24 through openings 30, as shown in FIG. 4B. In addition, vertical slot 26 can be closed in a second direction through body 24 so as to form closed sections 28, as shown in FIG. 1C. In an example, the first direction can be transverse or alternatively substantially perpendicular to the second direction. Vertical slot 26 can also optionally be cylindrical in shape. As shown in the cross-sectional view of FIG. 1C, this can create a situation in which walls of closed sections 28 of vertical slot 26 can be curved and conform to the curvature of a shaft 51 of spike 50, as described in more detail below. Stated differently, closed sections 28 can define walls of vertical slot 26 that have a radius of curvature that substantially conforms to or is substantially the same as a radius of curvature of spike 50. Still referring to FIG. 1C, closed sections 28 can also be completely closed along certain sections of vertical slot 26, for instance at locations where openings 30 are not present. At other areas, for example where openings 30 are formed, closed sections 28 can define walls that form partially cylindrical surfaces that have a radius of curvature that conforms to or is substantially the same as the radius of curvature of spike 50. Thus, in an example vertical slot 26 can form surfaces that conform to the shape of spike 50 to allow spike 50 to move longitudinally within vertical slot 26 in a controlled manner and accurately penetrate suture sections 90. As shown in FIG. 1C, vertical slot 26 can also intersect with the passage formed by openings 30.

In an alternate example, vertical slot 26 might not be cylindrical or partially cylindrical and instead can be any shape that matches or substantially conforms to the shape of spike 50 (e.g., oval, triangular, square, polygonal, etc.) In addition, in even further examples, vertical slot 26 can be shaped so as to "key" with spike 50. In other words, vertical slot 26 and spike 50 can take a shape so that spike 50 is rotationally locked or substantially rotationally locked relative to and within vertical slot 26. Vertical slot 26 can also have a proximal part or proximal end section that can be tapered to conform to tapering that might be present on a portion of spike 50 (e.g., its head 54).

It should be noted that breakable area 32 can extend proximally above a distal-most end of openings 30, as shown in FIG. 1C. As described in more detail in the context of the surgical method, this positioning can become important as spike 50 is driven through suture sections 90.

Suture anchor 10 can further include, near a proximal section 14 of anchor 10, a projection 21 that can have an external threaded surface 20 for interacting with a deployment instrument 70. Projection 21 can define an internal bore 18 leading to vertical slot 26. Interposed between vertical slot 26 and internal bore 18 can be a retaining cavity 22. Internal bore 18, in an example, can have a diameter that is slightly smaller than a cross-sectional diameter of a head 54 of spike 50 In addition, a proximal-most end of projection 21 can include a taper for facilitating insertion of head 54 into internal bore 18. Thus, as described in more detail below, the walls of internal bore 18 of projection 21 can provide an inward force on head 54—with its larger diameter—as it travels through internal bore 18. This inward force can cause the partial tube portions 58 to flex inward as head 54 moves through internal bore 18.

Alternatively, in another example, projection 21 might not be entirely cylindrical and instead can be a broken cylinder with two (2), three (3), or more than three (3) partially-cylindrical sections that are capable of flexing outwards. In other words, instead of being completely cylindrical as shown in the depicted example, projection 21 can form partially-cylindrical arms separated by vertical slots formed in a proximal-distal direction through projection 21. Such "arms" can be independent of each other and thereby be capable of flexing outwards as head 54 passes through internal bore 18. In addition, each arm can have an externally-threaded surface 20 that can, collectively, engage with deployment instrument 70 in the manner set forth below (i.e., via a screw-and-nut engagement).

A retaining cavity 22 can be positioned distally of internal bore 18, and can be dimensioned to receive head 54 of spike 50, as shown for example in FIG. 4B. As such, retaining cavity 22 can have a diameter or alternatively a maximum dimension that is greater than that of internal bore 18, such that a step 42 can be formed between retaining cavity 22 and internal bore 18. Step 42 can act to retain spike 50 in retaining cavity 22, as described more fully below. In addition, vertical slot 26 at its proximal-most end can be dimensioned to be smaller than head 54 of spike 50 so that head 54 cannot enter into vertical slot 26 after being received in retaining cavity 22.

Figure 2:
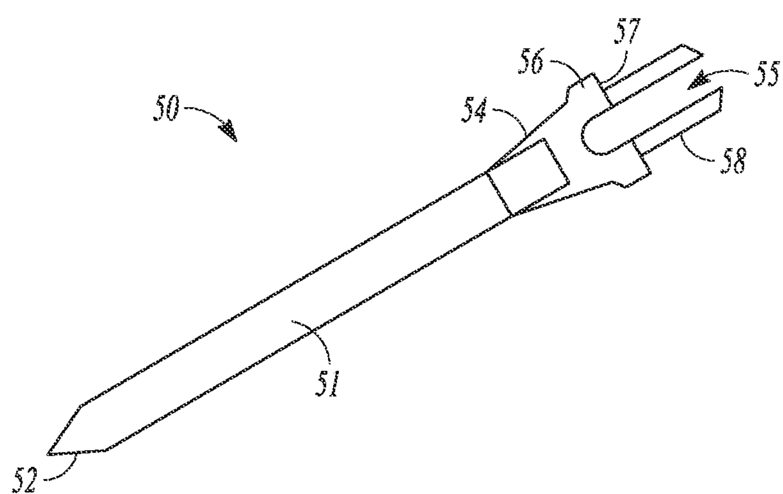
FIG. 2 illustrates a suture spike utilized with the knotless implant of FIGS. 1A and 1C.

An example of spike 50 is shown in FIG. 2. As illustrated, spike 50 can have a shaft 51 with a sharp tip 52 capable of puncturing suture sections 90. Shaft 51 can have a cross-sectional diameter that is slightly smaller than a cross-sectional diameter of vertical slot 26. In addition, in yet another example, shaft 51 can define a radius of curvature that conforms to or is the substantially the same as a radius of curvature of vertical slot 26.

Spike 50 can also include a head 54, which is optionally tapered. Head 54 can form a ring-like protrusion 56 that extends partially or entirely around a circumference of head 54 for engaging with step 42 of retaining cavity 22. In an example, a single protrusion 56 forming a ring around the circumference of head 54 can be present, although instead a single or multiple protrusions 56 that extend only partly around the circumference of head 54 can be included with spike 50. In the case of the depicted example of FIG. 2, multiple ring-like protrusions 56 (e.g., two (2)) can be provided, such that head 54 is bifurcated into two (2) halves. A first protrusion 56 can be present on a first half of head 54, and a second protrusion 56 can be present on a second half of head 54. Each half of head 54 can be formed via an opening 55 extending into and through head 55, as shown in FIG. 2. In the depicted example, each ring-like protrusion 56 can be separated from the other to collectively form a set of protrusions 56 that are capable of engaging step 42 of retaining cavity 22. Since, in an example, opening 55 can extend into head 54 distally of protrusions 56, some flexibility can be provided to head 54 to allow each half of head 54 to flex inward as head 54 travels through internal bore 18 of projection 21. Thus, each half of head 54 in an example can flex inward as head 54 travels through internal bore 18 and then can spring outwards into engagement with retaining cavity 22 to retain spike 50 in retaining cavity 22. In this regard, a cross-sectional diameter taken at the location of protrusion 56 can be greater than a cross-sectional diameter of internal bore 18, but slightly less than the cross-sectional diameter of retaining cavity 22.

Spike 50 additionally can have a complete or alternatively a partial tube 58 extending from head 54 for interacting with deployment instrument 70. As an example, a fully-cylindrical tube 58 can be present on head 54 or alternatively a series of partially-cylindrical tube portions 58 can be utilized. In the case of the depicted example, two (2) partially-cylindrical tube portions 58 can extend from head 54. Each partially-cylindrical tube portion 58 can extend from a half of head 58, with each tube portion 58 being separated by the extent of opening 55. Collectively, each partially-cylindrical tube portion 58 can therefore form a set that is capable of engaging with deployment instrument 70, in the manner described below. Additionally, each partially-cylindrical tube portion 58 can extend towards head 54 and terminate at a step 57 that engages with instrument 70 (and with step 42 of retaining cavity 22 when inserted therein).

Deployment instrument 70 is shown in FIGS. 1B, 3A-4B, and 5. Referring to FIG. 1B, deployment instrument 70 can have a handle 84, a hollow shaft 86, a button cover 72, and a button mechanism 76. As shown in FIG. 3B, shaft 86 of instrument 70 can be hollow and can have a distal-most end with an internally-threaded surface 88 for engaging with externally-threaded surface 20 of projection 21 of implant 10. When engaged therewith, the distal-most end of shaft 86 can abut a step 23 of implant 10. Hollow shaft 86 can have a cross-sectional diameter that is approximately the same as or only slightly greater than the cross-sectional diameter of head 54 of spike 50, at protrusions 56.

A pusher tube 80 can also be disposed in hollow shaft 86 of instrument 70. Pusher tube 80 can be a hollow tube 80 with an internal diameter that can be approximately the same as or slightly greater than an external diameter of partially-cylindrical tube portions 58. Thus, tube 80 can be placed over tube portions 58 and moved distally until pusher tube 80 reaches and engages step 57 of spike 50. At the same time, pusher tube 80 can have an external diameter that is less than an internal diameter of hollow shaft 86 so that pusher tube 80 can move longitudinally relative to and within shaft 86. In this regard, pusher tube 80 can be connected to button mechanism 76, as shown in FIGS. 3A-B. Actuation of button mechanism 76 can cause pusher tube 80 to move distally relative to and within hollow shaft 86, while releasing button mechanism 76 optionally can allow pusher tube 80 to move proximally. A button cover 72 and a latch 74 therefor can also be provided with instrument 70 to ensure that button mechanism 76 is covered during initial implantation of implant 10, and button mechanism 76 is not prematurely actuated.

In an example, although not shown, button mechanism 76 can be any mechanism capable of moving pusher tube 80 distally and/or proximally, as recognized by a person of skill in the art. As an example, button mechanism 76 can be a button connected by one (1) or more linkages to pusher tube 80, such that depressing button mechanism 76 causes pusher tube 80 to move distally. In addition, the linkages can be associated with a spring or other biasing mechanism, such that releasing button mechanism 76 causes the spring to actuate and force pusher tube 80 proximally. In an example, a catch or other mechanism, with a release, can be provided with instrument 70 so that button mechanism 76 can be depressed, engage with the catch, and subsequently be released via a release mechanism to return button mechanism 76 back to its initial condition. Other mechanisms for moving pusher tube 80 proximally and distally are, of course, contemplated.

In an example, deployment instrument 70 can also include a viewing aperture or slot 78 for confirming that button mechanism 76 has been fully deployed, thereby validating that pusher tube 80 has been fully advanced distally inside hollow shaft 86.

Methods of implanting implant 10 and performing a soft-tissue repair using implant 10 will now be disclosed. The methods set forth below are merely exemplary, and although certain steps may be set forth in a particular order, the order is not required and steps may be performed in a different order than set forth. The particular method below, used merely as an example, is a rotator cuff repair. It is contemplated, however, that suture anchor 10 can be used in any repair where soft tissue is to be drawn back to its natural condition in the body.

In an example, the method comprises first establishing an access portal through the skin and tissue of a shoulder of the patient (e.g., using a percutaneous cannula). Again, other anatomical locations are contemplated, such as repairs in the knee, hips, ankles, or other small bones. With the access portal established, one (1) or more sutures can be passed through the access portal to the surgical site and through the soft tissue, in this case the rotator cuff in the patient's shoulder. The one (1) or more sutures can be inserted through the soft tissue at one (1) or more locations. As an example, a suture can be placed through the soft tissue at two (2) locations to establish an inverted mattress stitch for a single-row repair. Many other suture configurations are possible, including where multiple sutures are used, such as the suture configurations used for double-row repairs or trans-osseous equivalent. A single-row repair is discussed below merely as an exemplary use of suture anchor 10, it being understood that other repairs are possible.

As shown in FIG. 3B, after placement of a suture through the soft tissue using an inverted mattress stich, two (2) suture sections 90 can extend from the soft tissue and form tissue-facing 92 and free end sides 94 of suture sections 90. Free ends 94 can be withdrawn from the access portal and threaded through large eyelet portion 34 of suture anchor 10 using suitable instrumentation, such as a loop of material used as suture threader. With free ends 94 of suture sections 90 through large eyelet portion 34, the surgeon can then grasp free ends 94 and insert suture anchor 10 through the access portal using deployment instrument 70. Suture anchor 10 can be pre-attached to deployment instrument 70 or the surgeon can attach suture anchor 10 to deployment instrument 70 after free ends 94 of suture sections 90 are drawn through large eyelet portion 34. In particular, internal threading 88 of shaft 86 of instrument can be threaded onto external threading 20 on projection 21 of suture anchor 10.

The surgeon can then grasp free ends 94 of suture sections 90 and use handle 84 of instrument 70 to insert suture anchor 10 through the access portal into the patient's shoulder. Free ends 94 of suture sections 90 can be tensioned by the surgeon to remove slack as suture anchor 10 is moved distally through the access portal towards the patient's torn rotator cuff. Previously, or at any point before suture anchor 10 is driven into bone, a suitable awl, pilot drill, or other instrument can be used by the surgeon to create an opening in bone of the patient for receiving suture anchor 10. In this case, the opening can be formed in the patient's humerus. Suture anchor 10 can then be positioned at the site of the bone opening and driven into the opening, distal pointed end 16 first, until anchor 10 is fully seated in the bone. In this regard, the surgeon can elect to use a mallet or other instrument to tap on a proximal end of deployment instrument 70 and cause suture anchor 10 to become embedded in the bone hole. Deployment instrument 70 can therefore also act as an insertion instrument for suture anchor 10. As suture anchor 10 is being inserted, barbs or spikes 12 can engage the walls of the bone hole, and optionally flex and provide an outward force sufficient to embed themselves in the bone and provide ample pull-out resistance for suture anchor 10.

With suture anchor 10 embedded in the bone hole, or optionally prior thereto, the surgeon can exert tension on free ends 94 of suture sections 90 and cause the portions of suture sections 90 extending through large eyelet portion 34 (e.g., the two (2) suture sections 90 of the single suture in the single-row repair context) to move towards small eyelet portion 36. Neck 38 between eyelets 34, 36 can be useful in this instance to draw suture sections 90 extending through large eyelet portion 34 towards and into small eyelet portion 36. Because small eyelet portion 36 can have a cross-sectional width that is only slightly larger than the width of suture sections 90, the parts of suture sections 90 extending through suture anchor 10 can become aligned in small eyelet portion 36. In other words, such suture sections 90 can become stacked linearly next to each other within small eyelet portion 36, similar to as shown in FIG. 4B where the aforementioned suture sections 90 are linearly aligned within vertical slot 26.

It should be noted that suture anchor 10 can be designed to allow tension to be applied to free ends 94 of suture sections 90 when anchor 10 is embedded in bone. Thus, there can be room between the walls of the bone hole and body 24 of suture anchor to allow tensioning of free ends 94 and movement of the suture or sutures relative to body 24.

As additional tension is applied to free ends 94 by the surgeon, and because tissue-engaging side 92 of suture sections 90 can be engaged with soft tissue, suture sections 90 extending through implant 10 can force themselves against breakable area 32 and cause breakable area 32 to fracture. Alternatively, as contemplated in the different examples above, breakable area 32 can instead be pre-broken, open, or utilize any other features set forth herein to allow the aforementioned parts of suture sections 90 to pass by breakable area 32 upon the application of a sufficient amount of force/tension. At such point, the aligned parts of suture sections 90 can travel into vertical slot 26 of suture anchor 10, where such suture sections 90 can remain aligned. Indeed, since vertical slot 26 can have a maximum dimension that is anywhere between one-hundred to one-hundred and ninety five percent (100-195%), more preferably one-hundred to one-hundred and fifty percent (100-150%) of the cross-sectional diameter of the suture, each suture section 90 can remain substantially linearly aligned within vertical slot 26.

At this stage, the surgeon can elect to apply further tension to free ends 94 to draw the soft tissue, in this instance the patient's rotator cuff, back into its normal anatomical position. As an example, the patient's rotator cuff can be drawn back into position against the humerus so that the rotator cuff properly reattaches to the humerus during healing (e.g., in the case of a tear where the rotator cuff has detached).

After sufficient tension is applied and the soft tissue tear is reduced, the surgeon can use deployment instrument 70 to deploy spike 50 through suture sections 90 extending through vertical slot 26 to fix such sections 90 relative to implant body 24 and complete the repair. In an example, the surgeon can open button cap 72 and depress button mechanism 76 to cause pusher tube 80 to move distally within hollow shaft 86. Because pusher tube 80 can contact step 57 of spike 50 inside hollow shaft 86, such distal movement of pusher tube 80 can cause spike 50 to advance distally within hollow shaft 86 until it enters implant 10, in particular inner bore 18 of projection 21. A press-fit can be established between pusher tube 80 and tube portions 58 on spike 50 so that spike 50 can be moved easily proximally and/or distally within hollow shaft 86.

Figure 6:
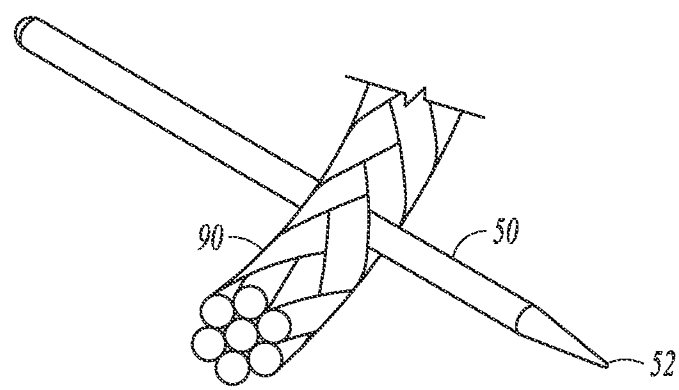
FIG. 6 is a perspective view of a suture spike in accordance with an example of the disclosure after being driven through one (1) or more sutures.

With further distal advancement of pusher tube 80, head 54 and in particular protrusions 56 thereof can advance into inner bore 18. Head 54 of spike 50 and/or projection 21 of implant 10 can flex at this point to accommodate the dimensional differences between protrusions 56 of spike 50 and inner bore 18 of projection 21 (e.g., the cross-sectional diameter of head 54 at protrusions 56 being greater than the cross-sectional diameter of inner bore 18). At the same time, sharp tip 52 of spike 50 can penetrate suture sections 90 extending through vertical slot 26. A schematic example of a spike 50 penetrating a braided suture is shown in FIG. 6. As shown, spike 50 can, more or less, become inserted through and/or between the braid strands of suture sections 90 and not damage the integrity of suture sections 90 to any appreciable degree. Alternatively, it is of course contemplated that non-braided sutures (e.g., monofilaments) or any other type of suture could be used and spike 50 could penetrate the same without damage to the suture's structural integrity.

Figure 4A:
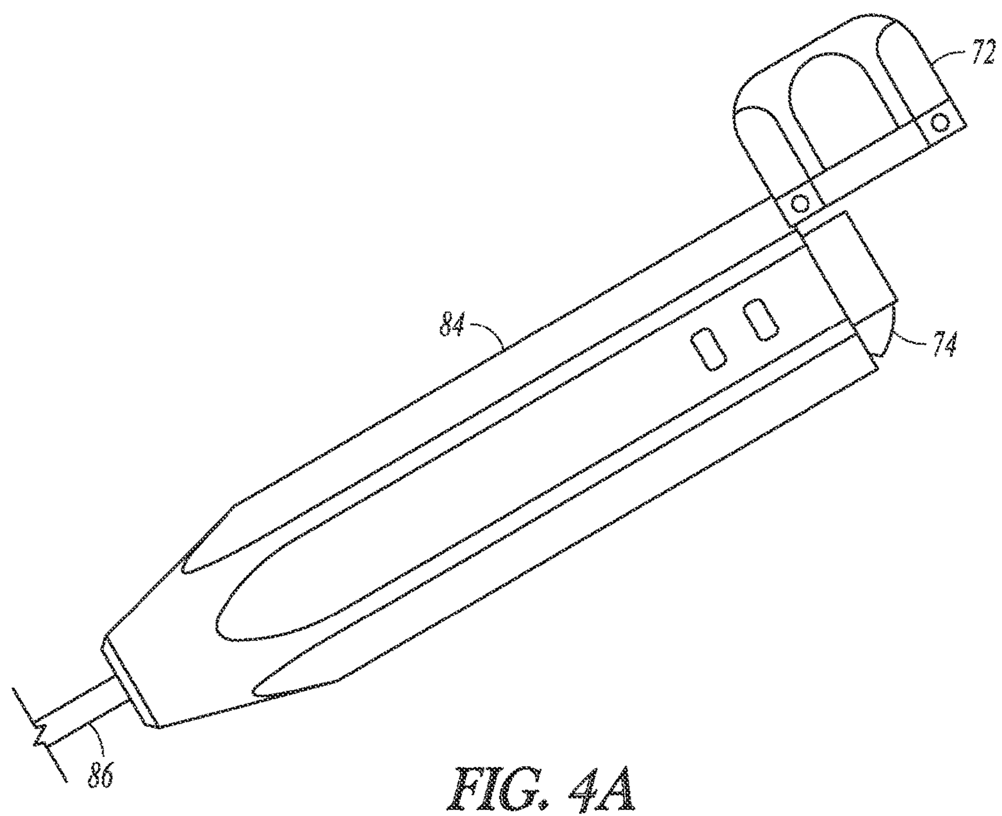
FIG. 4A is a perspective view of the handle of the deployment instrument of FIG. 1B shown in a deployed state.
Figure 4B:
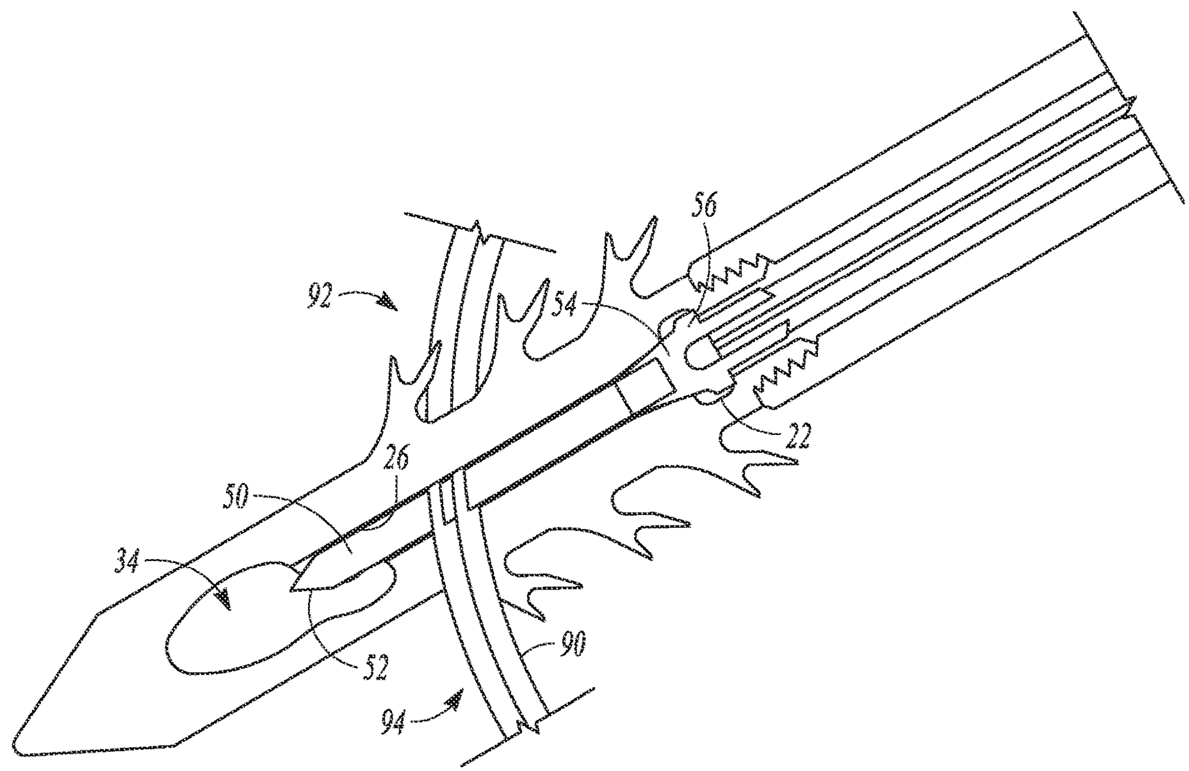
FIG. 4B is a cross-sectional view of the knotless implant of FIG. 1A shown in a corresponding deployed state.
Figure 5:
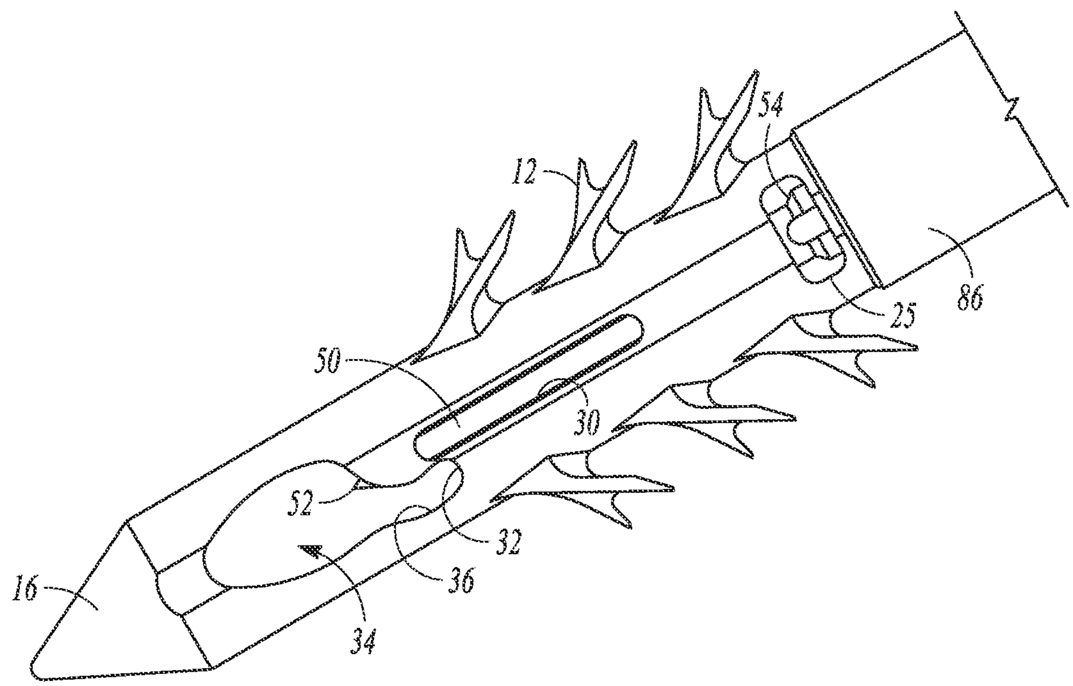
FIG. 5 is a side view of the knotless implant of FIG. 4B in the deployed state.

Referring to FIGS. 4A-B, with button mechanism 76 fully depressed, head 54 of spike 50 can become seated in retaining cavity 22 of suture anchor 10 and be prevented from moving further distally due to a dimensional interference between head 54 and vertical slot 26. In particular, as head 54 moves distally in inner bore 18, ultimately protrusions 56 can pass step 42 of retaining cavity 22 and protrusions 56 can snap into position within retaining cavity 22. In other words, head 54 of spike 50 can have sufficient room to become unflexed in retaining cavity 22, allowing protrusions 56 to expand outwards in retaining cavity 22. At this point, spike 50 cannot back out of body 24 of implant 10 due to interference between step 57 of spike and step 42 of retaining cavity 22, and spike 50 cannot move significantly in a distal direction due the fact that vertical slot 26 is smaller in width than head 54. If spike 50 were moved proximally, steps 42, 57 would engage and prevent spike 50 from withdrawing out of implant 10. At this stage, suture sections 90 can become fixed relative to suture anchor 10, in a knotless manner, due to spike 50 penetrating suture sections 90 extending through vertical slot 26. The linear alignment of suture sections 90 in vertical slot 26 can facilitate penetration by spike 50. Thus, the patient's soft tissue is repaired in a reliable and knotless manner.

It should be noted that spike 50 can provide for a situation in which it is virtually impossible for suture sections 90 to slide relative to suture anchor 10 once spike 50 is driven through suture sections 90. This is in contrast to certain suture anchors, which utilize an internal screw to bear upon a suture extending through the suture anchor to fix the suture relative to the anchor. In these situations, the suture is only fixed via friction between the internal screw of the anchor and the anchor itself. The suture could therefore suffer from slippage if the friction fit is insufficient, if enough force is borne on the suture after implantation, and/or if the internal screw loosens. With the present suture anchor 10, suture sections 90 cannot slip relative to suture anchor 10 as suture sections 90 can be penetrated with spike 50 and are not fixed merely by friction.

Lastly, the surgeon can unscrew deployment instrument 70 from the deployed suture anchor 10 and withdraw deployment instrument 70 out of the access portal in the patient's shoulder. Additionally, the surgeon can trim any excess suture material resulting from free ends 94 of suture sections 90 extending outside of the bone hole. The repair can then be completed.

In the devices shown in the figures, particular structures are shown as being adapted for use as a suture anchor or in a method of implantation thereof. The disclosure also contemplates the use of any alternative structures for such purposes, including structures having different lengths, shapes, and/or configurations. For example, although suture spike 50 is shown as being non-threaded, other examples using different deployment and/or locking techniques can use a threaded suture spike 50. As an example, in an alternate example suture anchor 10 can omit the structure of inner bore 18 and/or retaining cavity 22 in favor of using a threaded locking and/or advancement mechanism. As yet another example, a bayonetted locking mechanism can be used instead of retaining cavity 22. In the threaded example, part of shaft 51 of spike 50 can be threaded and, likewise, portions or all of vertical slot 26 can be threaded. To advance threaded spike 50, the surgeon can simply insert threaded spike 50 into engagement with threaded vertical slot 26 and rotate spike 50 so that spike 50 distally advances within vertical slot 26 to puncture suture sections 90. The threaded engagement between spike 50 and vertical slot 26 can also prevent spike 50 from withdrawing out of vertical slot 26, and thus implant 10.

Alternatively, threading can be applied only to a portion of spike 50 (e.g., its head 54) and, likewise, threading can be applied only to a portion of vertical slot 26 (e.g., a proximal part thereof). Spike 50 can then be driven through suture sections 90 by a pushing motion, without rotation, and then locked relative to implant via threading head 54 of spike 50 into the threaded part of vertical slot 26. Other locking and/or advancement mechanisms for spike 50 are also contemplated, of course. In addition, as noted in more detail above, spike 50 can alternatively be non-threaded and keyed to the shape of vertical slot 26 so that spike 50 cannot rotate relative to implant 10 as it is being driven through suture sections 90.

In a further example, spike 50 can be omitted altogether and a different locking mechanism for suture sections 90 can be used. As an example, certain structures can be utilized within vertical slot 26 to lock suture sections 90 relative to suture anchor 10 in a lateral direction. In an example, such structures could be a set of tapered surfaces that come closer together proximally in vertical slot 26, such that, as suture sections 90 move proximally in vertical slot 26, sections 90 engage the tapered surfaces of vertical slot 26 and become fixed via friction and/or compression relative to suture anchor 10. In this example, the aforementioned tapered surfaces can also use friction-increasing techniques to improve the locking of suture sections 90. As an example, the tapered surfaces can be roughened, ribbed, or include ridges that dig into suture sections 90 as they are pulled proximally in vertical slot 26. Thus, vertical slot 26 can employ other locking mechanisms for suture sections 90.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims.

It will also be appreciated that the various dependent claims, examples, and the features set forth therein can be combined in different ways than presented above and/or in the initial claims. For instance, any feature(s) from the above examples can be shared with others of the described examples, and/or a feature(s) from a particular dependent claim may be shared with another dependent or independent claim, in combinations that would be understood by a person of skill in the art.

What is claimed is:

1. A method of repairing a tear in human tissue comprising:
- passing a suture through soft tissue of a patient and through an eyelet of a suture anchor;
- implanting the suture anchor into an opening formed in a bone of the patient;
- tensioning a free end of the suture to move the soft tissue and at least partially reduce the tear;
- moving a shaft relative to and within the suture anchor so that the shaft penetrates through the suture and fixes the suture relative to the suture anchor; and
- applying a predetermined amount of tension to the free end of the suture so that the suture moves from the eyelet into a separate passage extending through the suture anchor.

2. The method of claim 1, wherein the shaft includes a sharp portion and the method comprises penetrating the suture with the sharp portion.

3. The method of claim 1, further comprising locking the shaft relative to the suture anchor.

4. The method of claim 1, further comprising preventing the suture from moving from the eyelet into the separate passage if the predetermined amount of tension on the free end of the suture is not met.

5. The method of claim 1, further comprising:
- passing multiple suture strands through the eyelet;
- tensioning free ends of the suture strands so that the suture strands move from the eyelet into the separate passage and become aligned within the separate passage; and
- moving the shaft relative to and within the suture anchor so that the shaft penetrates through the suture strands and fixes the suture strands relative to the suture anchor.

6. The method of claim 1, wherein moving the shaft relative to and within the suture anchor so that the shaft penetrates through the suture includes inserting the shaft between a plurality of braid strands of the suture.

7. A method of repairing a tear in human tissue comprising:
- passing a suture through soft tissue of a patient and through an eyelet of a suture anchor;
- implanting the suture anchor into an opening formed in a bone of the patient;
- tensioning a free end of the suture to move the soft tissue and at least partially reduce the tear;
- moving a shaft relative to and within the suture anchor until the shaft penetrates through the suture;
- further moving the shaft distally relative to the suture anchor until a protrusion on the shaft becomes retained in a retaining cavity of the suture anchor; and
- applying a predetermined amount of tension to the free end of the suture so that the suture moves from the eyelet into a separate passage extending through the suture anchor.

8. The method of claim 7, wherein the protrusion is located at a proximal end portion of the shaft.

9. The method of claim 7, wherein the shaft includes a sharp portion and the method comprises penetrating the suture with the sharp portion.

10. The method of claim 7, further comprising locking the shaft relative to the suture anchor.

11. The method of claim 7, further comprising preventing the suture from moving from the eyelet into the separate passage if the predetermined amount of tension on the free end of the suture is not met.

12. The method of claim 7, further comprising:
- passing multiple suture strands through the eyelet;
- tensioning free ends of the suture strands so that the suture strands move from the eyelet into the separate passage and become aligned within the separate passage; and
- moving the shaft relative to and within the suture anchor so that the shaft penetrates through the suture strands and fixes the suture strands relative to the suture anchor.

13. The method of claim 7, wherein the retaining cavity includes a step, and wherein the protrusion is engageable with the step in the retaining cavity to prevent the shaft from withdrawing proximally out of the suture anchor.

14. A method of repairing a tear in human tissue comprising:
- passing one or more sutures having multiple suture strand sections through soft tissue of a patient and through an eyelet of a suture anchor, the suture anchor further including a separate passage extending in a longitudinal direction through the suture anchor, the eyelet and the separate passage forming a junction therebetween;
- implanting the suture anchor into an opening formed in a bone of the patient;
- tensioning the one or more sutures;
- aligning the multiple suture strand sections in the suture anchor;
- moving a shaft relative to and within the suture anchor until the shaft penetrates through the multiple suture strand sections to fix the multiple suture strand sections relative to the suture anchor; and applying a predetermined amount of tension to a free end of the one or more sutures so that the multiple suture strand sections move from the eyelet into the separate passage.

15. The method of claim 14, further comprising: moving the shaft further distally relative to the suture anchor until a protrusion on a proximal end of the shaft becomes retained in a retaining cavity of the suture anchor.

16. The method of claim 14, wherein the shaft includes a sharp portion and the method comprises penetrating the multiple suture strand sections with the sharp portion.

17. The method of claim 14, further comprising locking the shaft relative to the suture anchor.

18. The method of claim 14, further comprising preventing the multiple suture strand sections from moving from the eyelet into the separate passage if the predetermined amount of tension on the free end of the one or more sutures is not met.

* * * * *